US006825927B2

(12) United States Patent
Goldman et al.

(10) Patent No.: US 6,825,927 B2
(45) Date of Patent: Nov. 30, 2004

(54) CONTROLLER FOR A FLUOROMETER

(75) Inventors: Jeffrey A. Goldman, Acton, MA (US);
Igor Kordunsky, Newton, MA (US);
Khalid M. Aboushhiwa, Belmont, MA
(US); Robert Alan Iovanni, Raymond,
NH (US)

(73) Assignee: MJ Research, Inc., Waltham, MA (US)

( * ) Notice: Subject to any disclaimer, the term of this patent is extended or adjusted under 35 U.S.C. 154(b) by 73 days.

(21) Appl. No.: 10/170,662

(22) Filed: Jun. 12, 2002

(65) Prior Publication Data

US 2003/0016352 A1 Jan. 23, 2003

Related U.S. Application Data

(60) Provisional application No. 60/298,657, filed on Jun. 15, 2001.

(51) Int. Cl.$^7$ .............................. G01J 3/30; G01N 21/64
(52) U.S. Cl. ..................................... 356/317; 250/458.1
(58) Field of Search ................................ 356/317–318, 356/417; 250/458.1–461.2

(56) References Cited

U.S. PATENT DOCUMENTS

| | | | |
|---|---|---|---|
| 4,804,850 A | 2/1989 | Norrish et al. ............ 250/459.1 |
| 5,210,015 A | 5/1993 | Gelfand et al. ................. 435/6 |
| 5,315,993 A | 5/1994 | Alcala ......................... 128/634 |
| 5,928,907 A | 7/1999 | Woudenberg et al. ..... 435/91.2 |
| 5,994,056 A | 11/1999 | Higuchi ......................... 435/6 |
| 6,015,534 A | 1/2000 | Atwood ...................... 422/102 |
| 6,015,674 A | 1/2000 | Woudenberg et al. ......... 435/6 |
| 6,043,880 A | 3/2000 | Andrews et al. ............. 356/311 |
| 6,084,667 A * | 7/2000 | Melman et al. .............. 356/246 |
| 6,140,054 A | 10/2000 | Wittwer et al. ................. 435/6 |
| 6,144,448 A | 11/2000 | Mitoma ....................... 356/317 |
| 6,174,670 B1 | 1/2001 | Wittwer et al. ................. 435/6 |
| 6,337,435 B1 | 1/2002 | Chu et al. .................... 136/242 |
| 6,340,589 B1 | 1/2002 | Turner et al. ............. 435/287.2 |
| 6,369,893 B1 * | 4/2002 | Christel et al. ............. 356/417 |
| 6,373,568 B1 * | 4/2002 | Miller et al. ................. 356/326 |
| 6,403,970 B1 * | 6/2002 | Hung ......................... 356/317 |
| 6,498,440 B2 * | 12/2002 | Stam et al. ................. 315/291 |

FOREIGN PATENT DOCUMENTS

WO          WO01/35079 A1      5/2001

* cited by examiner

Primary Examiner—Zandra Smith
Assistant Examiner—Kara Geisel
(74) Attorney, Agent, or Firm—Lahive & Cockfield, LLP.

(57) ABSTRACT

A method and apparatus relating to a controller for controlling a light emitting array by setting a power level provided to each individual light emission source within the light emitting array is provided. The controller includes a processor for executing instructions and a memory device for storing data. The data from the memory device provides individual instruction for a power level required for each individual light emission source to achieve a normalized detection of light within the fluorometer. A method of manufacturing a controller for controlling the emission of light in a fluorometer includes analyzing the well values of illumination and storing power level values in a memory device corresponding to predetermined illumination levels of the illumination sources.

19 Claims, 7 Drawing Sheets

CONTROLLER FOR A FLUOROMETER

RELATED APPLICATION

This application claims priority to co-pending U.S. Provisional Application No. 60/298,657 filed Jun. 15, 2001, for all subject matter common to both applications. The disclosure of said provisional application is hereby incorporated by reference in its entirety.

FIELD OF THE INVENTION

The present invention relates to the generation of excitation light in a system for detecting fluorescence emission, and more particularly to a control method for an apparatus for measuring fluorescence levels in samples.

BACKGROUND

The extent or rate of certain known chemical reactions can be measured by the alteration of levels of fluorescence when samples are illuminated by a suitable source of light. Likewise, some chemical and biological samples couple to fluorescent reporters such that measurement of fluorescence provides useful information regarding the makeup or quantity of the particular sample. Hence, devices for measuring and analyzing fluorescence are known in the art.

The basic process for illuminating and measuring fluorescence can be generally described as follows. A sample to be analyzed is placed in a suitable optical vessel such as a position or a well in a multiwell array. A source of light of suitable wavelength, such as an LED, a laser, or a lamp is directed toward the sample to excite the fluorescent molecules of the sample. The fluorescent molecules then emit light, which is read by an optical sensor. Certain characteristics of the emitted fluorescent light can be analyzed, and a scientific result obtained with regard to the nature or quantity of the particular sample.

An "excitation light source" as utilized herein is intended to generally mean a source of light of a restricted wavelength range suitable for the excitation of fluorescence. Example excitation light sources include one or more light-emitting diodes, a combination of one or more light-emitting diodes and an optical filter, a combination of an incandescent light source and an optical filter, a combination of a fluorescent tube light source and an optical filter, and a laser such as a diode laser.

An "emission light detector" as utilized herein is intended to generally mean a light sensor coupled with any necessary optical filters so as to be useful for detection of fluorescent emission, while being essentially insensitive to light at the excitation wavelength. This may include an amplifier circuit and other associated electronics.

The combination of conventional fluorometers with conventional thermal cyclers is known in the field of molecular biology. For instance, such instruments are described in U.S. Pat. Nos. 5,928,907, 6,015,674, 6,043,880, 6,144,448, 6,337,435, and 6,369,893. It is useful to create such combinations to perform different types of analysis. Some example applications and combinations can be found in U.S. Pat. Nos. 5,210,015, 5,994,056, 6,140,054, and 6,174,670. In typical procedures, fluorescence measurements are made during or after the Polymerase Chain Reaction ("PCR") process to quantify or identify target DNA.

The invention is directed toward a particular class of fluorometers, disclosed in PCT Application Publication Number WO 01/35079 to E.I. DuPont De Nemours and Company, filed Nov. 9, 2000, which is hereby incorporated in its entirety by reference. FIG. 1 illustrates the elements that combine to form a basic fluorometer 10. The fluorometer 10 includes a supporting structure 12. A sample 14 for analysis resides in a position in the form of a well 16 of the fluorometer 10. The sample 14 is commonly in liquid form, but can be in other physical states. An excitation light source, such as one or more LEDs 18, directs excitation light to well 16 along approximately axis A—A. The excitation light illuminates the sample 14. The incident light excites fluorophores in the sample 14 and causes the fluorophores to fluoresce, emitting light of a relatively longer wavelength than the incident light. A portion of the emitted light is collected by an emission light detector, which can include a photomultiplier tube (PMT) 20. The PMT 20 converts the light into an electrical signal. For each sample well 16, there is a distinct excitation light source 18 so that multiple wells can be separately illuminated.

The amount of fluorescence emitting from a particular well 16 filled with the sample 14 is generally proportional to the amount of excitation light directed toward that well 16. In conventional fluorometers of similar design, the amount of excitation light reaching each well is not well controlled. More specifically, in the device described in PCT Application WO 01/35079, the amount of current driving each LED is substantially equal. However, differences in the efficiencies of individual LEDs result in different amounts of light output, and differences in the geometry of the excitation light path result in differences in the fraction of the excitation light that reaches each well. Furthermore, the efficiency of detection of fluorescence emission light varies depending on the geometry of the path from the sample well to the emission light detector.

The combination of these factors results in the need to calibrate each well by multiplying the fluorescence measurement of each well by a normalization factor. The result of such a correction is that the sensitivity and noise levels of each well vary as a function of well location, which can be undesirable. In addition, the accuracy of the resulting data is somewhat compromised, and small errors in measurement can be greatly amplified by multiplying the data by the normalization factors.

BRIEF DESCRIPTION OF THE DRAWINGS

The features and aspects of the present invention, will become better understood with regard to the following description and accompanying drawings, wherein.

DETAILED DESCRIPTION

Figure 1:
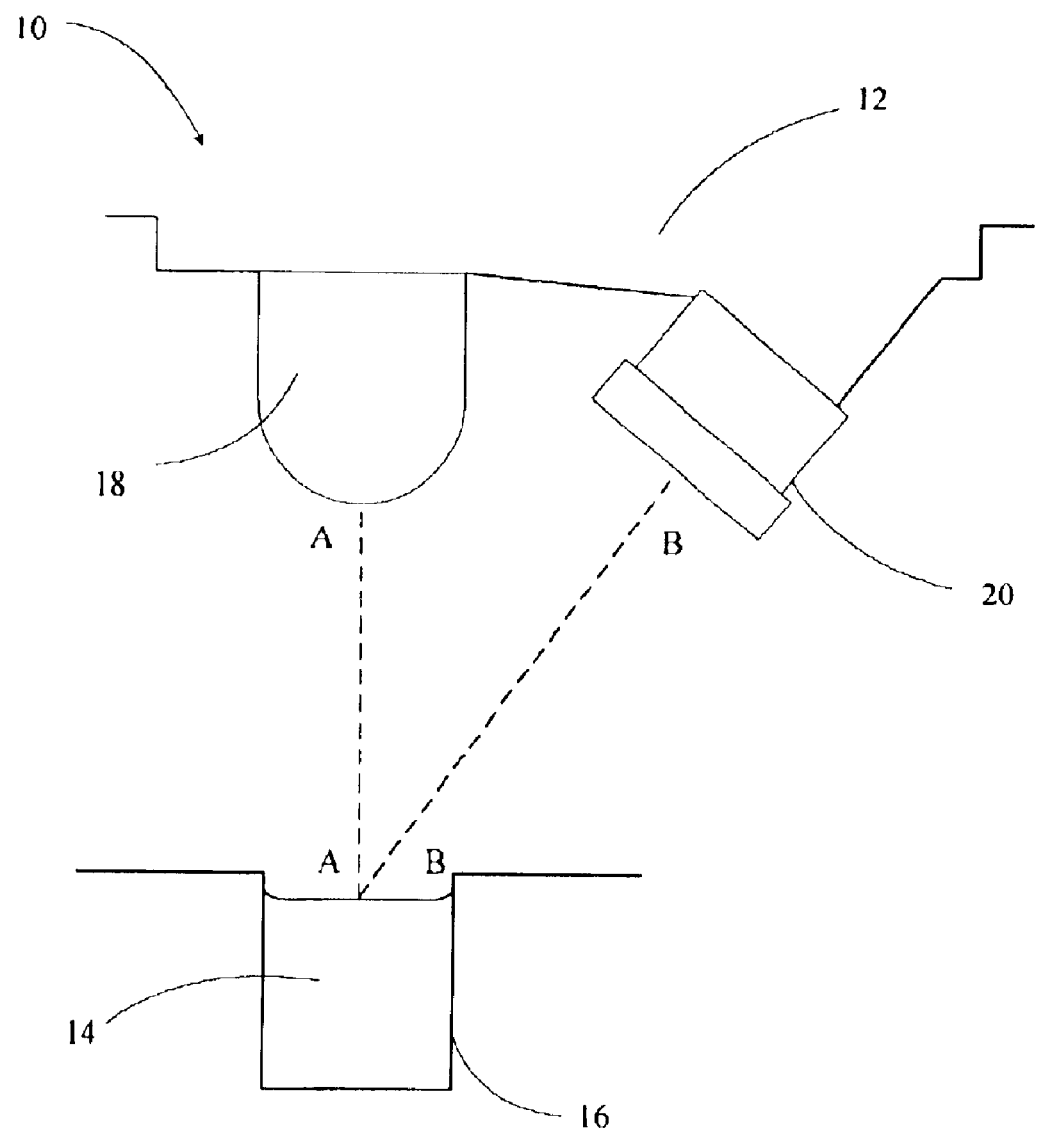
FIG. 1 is a diagrammatic illustration of a prior art configuration for detection of fluorescence emission.

An illustrative embodiment of the present invention relates to a controller for controlling the generation of light from an array of excitation light sources. According to one aspect of the present invention, an array of excitation light sources is disposed opposite an array of wells such that each individual excitation light source correlates to, and illuminates, an individual well. Each individual well is sized and dimensioned to contain a sample. The sample typically includes some fluorophore. A method of the present invention determines the electrical current required for supply to each excitation light source individually, such that the light generated by each excitation light source is substantially at a level predetermined for that particular source. In one embodiment, these levels are determined during instrument manufacture. In one embodiment, the predetermined light levels are set such that an equal amount of fluorophore in the samples generates a substantially equal amount of signal at the emission light detector, i.e., detection efficiencies are normalized for the samples.

In accordance with the teachings of the present invention, signal levels corresponding to each well are equalized. The equalization of signal levels obviates downstream processing of the data from the different wells to obtain normalized response. A detector linear range for each well is also equalized. Further, detector noise and all post detector noise is substantially equal for all wells. Because the signal is equalized and the noise is equalized, a signal-to-noise ratio is also equalized for all wells. Since signal-to-noise ratios are substantially equal, and detector linear range is substantially equal for all wells, the upper and lower limits of detection should also be substantially equal for all wells.

The present invention, in accordance with one embodiment, utilizes an EEPROM (electrically erasable programmable read only memory) to contain values that translate into the desired power level of each individual excitation light source. When an excitation light source is switched to an "on" state, a D/A converter reads the value stored in the EEPROM to instruct a current amplifier and power the excitation light source accordingly.

FIGS. 2 through 7, wherein like parts are designated by like reference numerals throughout, illustrate an example embodiment and related aspects of a controller for a light emitting array according to the teachings of the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

Figure 2:
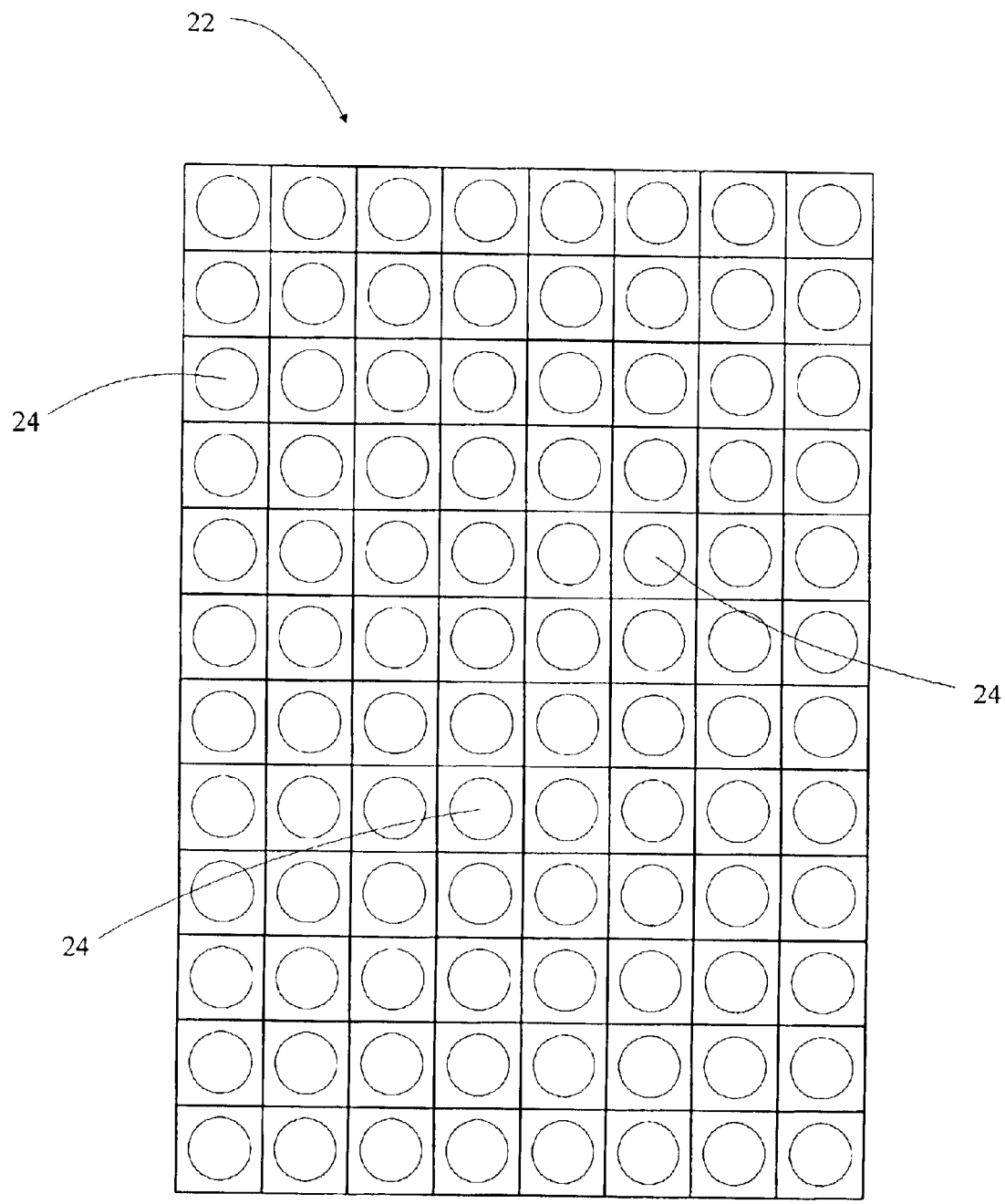
FIG. 2 is a diagrammatic illustration of an excitation light source array according to one embodiment of the present invention.

FIG. 2 illustrates an excitation light source array in the form of an LED array 22, formed from a collection of LEDs 24. The excitation light sources can take the form of any number of different sources for generating light, such as laser diodes, incandescent, fluorescent tube, flash tube, and the like. For purposes of clarity, the example of an LED excitation light source will be used for illustrative purposes herein. However, other excitation light sources may be used as understood by one of ordinary skill in the art. The particular LED array 22 illustrated represents an 8×12 array containing 96 individual LEDs 24. Typical blue or blue-green LEDs used for this purpose are available from vendors such as Cree Research of Durham N.C., Toshiba America of New York N.Y., or Nichia America of Southfield Mich.

Figure 3:
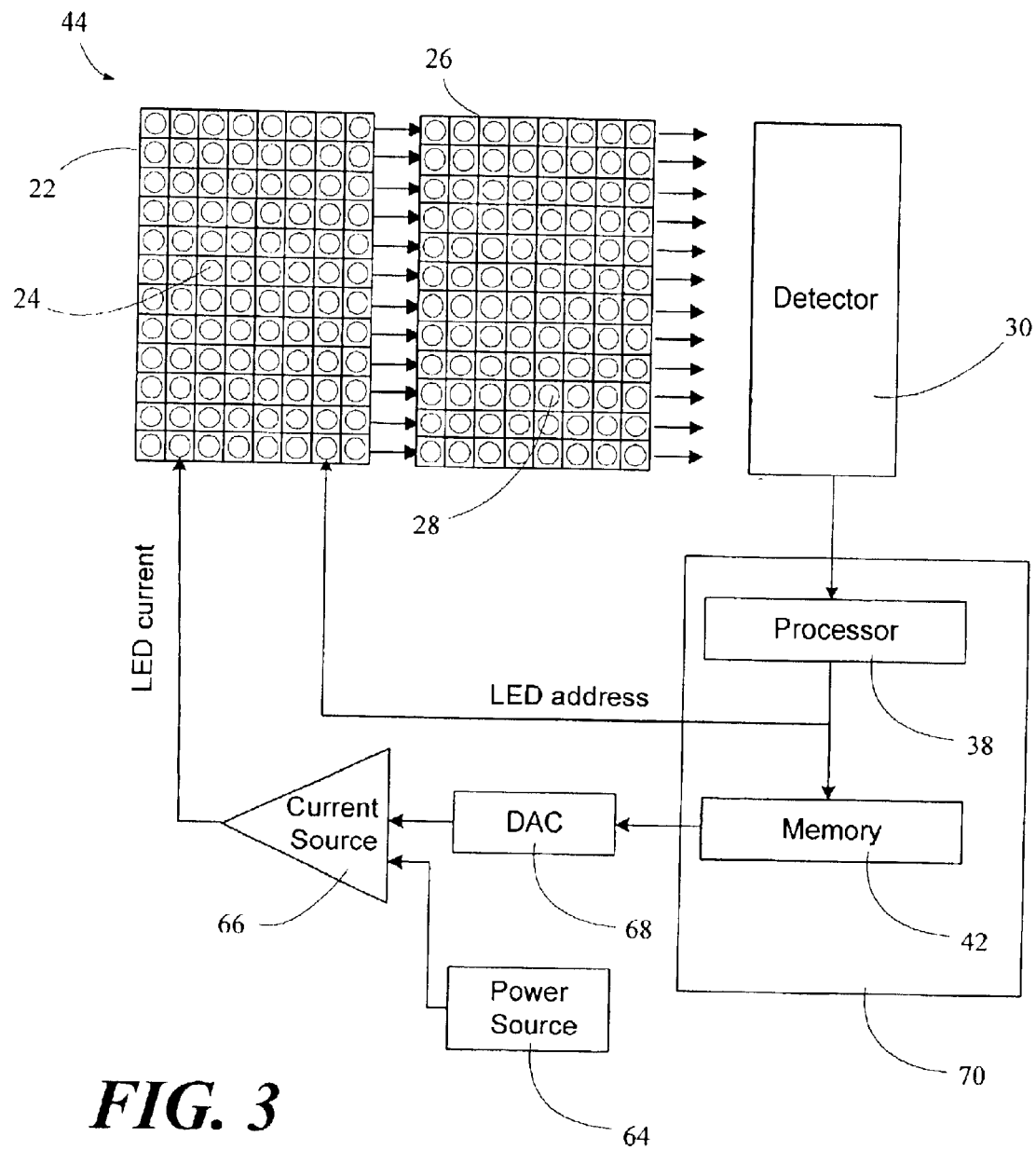
FIG. 3 is a diagrammatic illustration of a controller according to one aspect of the present invention.

The LED array 22 is disposed opposite a multiwell plate, tray, or collection of individual vessels containing individual positions in the form of wells 28 (see FIG. 3). Multi-well sample vessels are well known in the art, including those described in U.S. Pat. No. 6,340,589. Such vessels are known as microplates, and typically have sample wells disposed in a grid pattern with the X and Y grid spacing being an integer multiple or integer fraction of 9 mm. Individual sample vessels compatible with the microplate format are also known, for example as those described in U.S. Pat. No. 6,015,534. Most typically, there are 96 wells in an 8×12 grid array with grid spacing of 9 mm. Each LED 24 correlates with a specific individual well 28 of a sample tray 26.

One of ordinary skill in the art will also understand that the structure of the 8×12 array format is merely one of commonality within the experimental community that makes use of such devices as the present invention. However, the size, shape, and number of the arrays in each instance of LED, well, and optical sensor, can vary substantially. There can even be variation with regard to the relative numbers of elements in each array.

FIG. 3 illustrates a fluorometer 44 according to one embodiment of the present invention. In normal usage, each well 28 may contain a sample that a corresponding LED 24 illuminates. The sample typically includes fluorophores, such that the excitation by the LED 24 causes the sample to fluoresce. The aforementioned blue LED is particularly useful in conjunction with fluorescent dyes such as SYBR Green I available from Molecular Probes, Inc. of Eugene, Oreg., or carboxyfluorescein (FAM), which is available from many different sources. If other fluorescing materials are used in the sample, an LED generating a different color of light may be used.

The fluorescent emission light from the sample in the well 28 is detected using an emission light detector 30, which may include a photomultiplier tube (PMT). When photons impact the photo cathode, an electron cascade is generated, which results in a measurable electric current. PMTs are available from Hamamatsu Corporation of Bridgewater N.J. In this embodiment, the emission light detector 30 collects light from all of the wells 28 simultaneously. The LED array 22 illuminates the wells 28 individually, so that the fluorescence from each well 28 can be individually measured.

The emission light detector 30 can take the form of a number of different technologies, such as but not limited to photodiode, avalanche photodiode, photomultiplier tube, or a charge coupled device type camera. A processor 38 has a communication link with a memory device 42. The memory device 42 can be in the processor 38, or on the same card as the processor 38, or separate from the processor 38 with a communications link. The memory device 42 can take the form of, for example, an EEPROM. The combination of the processor 38 with the EEPROM forms a substantial portion of a controller 70 for operating the LED array 22 in accordance with the present invention. It should also be noted that although an EEPROM is used in this embodiment, that it is not an essential part of the control system and is added for convenience. It is possible to store data corresponding to LED power levels in other non-volatile memory devices, such as a hard drive, or directly in the RAM or SRAM of the processor 38.

The memory device 42, as programmed during the manufacturing process, contains the power level settings for each individual LED 24 to achieve the desired excitation or fluorescence levels, such as the example state of uniform fluorescence. The processor 38 identifies which LED 24 to illuminate, and addresses the memory device 42. The information, or data, in the memory device 42 instructs a current source 66, via a digital-to-analog converter 68, to provide the appropriate power levels drawn from a power source 64 for each LED 24 within the LED array 22. The processor 38 can include a typical general-purpose programmable device such as a microprocessor, micro-controller, digital signal processor, or personal computer, and can also include combination with accessory circuitry, such as digital-to-analog converters, analog-to-digital converters, and the like. Alternatively, the processor 38 need not include a general-purpose device, but may instead include a digital logic device, such as a programmable gate array, an application-specific integrated circuit, or a collection of discrete logic circuits such as counters, timers, and latches. In the instance of the processor including several components, a device in communication with one or more of the several components is considered to be in communication with the processor. The processor 38 can illuminate each LED 24 individually, sequentially, simultaneously, randomly, in sub-combination, or the like. If there are fewer wells 28 or samples than there are LEDs 24, each LED 24 lacking a corresponding active well 28 can be programmed not to illuminate. Those skilled in the art will appreciate that such devices can be programmed to perform the functions described herein. The processor 38 is capable of selecting an LED, obtaining data in a known sequence from the memory device 42, providing the data directly or indirectly to a current source 66, and causing individual excitation light sources 24 to be powered according to the data.

The resulting fluorometer 44 includes an LED array 22 that emits light, and produces a uniform fluorescent response as measured by the emission light detector 30 when applied to a uniform array of fluorophore-containing samples as directed by the controller 70. This uniform fluorescent response is referred to as a "normalized detection efficiency" for the samples. The predetermined, pre-programmed power levels resident in the memory device 42, e.g., the EEPROM, maintain a record of the power levels to each individual LED 24 of the LED array 22, such that the uniform fluorescence response can be easily replicated each time the fluorometer 44 is in use. Because the fluorescence sensitivity levels are substantially equal, or uniform, there is no need to multiply resulting optical signals by normalization factors to simulate a uniform excitation. In addition, if other fluorescence sensitivity patterns are desired, they can be additionally programmed into the memory device 42 and stored in the same manner for repeated operations.

One of ordinary skill in the art will understand that a further addition of lenses and filters added to the fluorometer 44 will aid in better focusing and processing the light emitted from the LED array 22. Applicants have not included such elements so as to more clearly present the novel features of the present invention. Such elements can, however, be used in conjunction with the present invention to achieve a more precise instrument.

It should be noted that the memory device 42 of the controller 70 can contain multiple profiles of excitation. For example, a first profile can generate a uniform fluorescence response across the entire array. A second profile can alternate active LEDs. A third profile can cause one half of the array to have high intensity, and the other half of the array to have a lower intensity. Additional profiles can are anticipated. The number of different profiles is limited by the size and form of the memory device 42. Each of the profiles can be programmed during the manufacturing and calibration of the fluorometer. Alternatively, an active communication with a processor can make use of the memory device 42 to initiate a specific profile, and then allow a user to modify that profile for each experiment, changing the LED intensities as desired.

Although the embodiment described uses an array of light sources as the means of individually illuminating the samples, it is recognized that the same concept of controlling the source intensity to adjust the fluorescence response of individual samples could apply to a single light source. In such an instance, the single light source can modulate the intensity to correspond with sequential measurements of samples.

In typical operation, light from the LED array 22 individually illuminates each sample well 28 of the tray 26 in sequence. The incident light excites the fluorophores in the wells 28, and the resulting fluorescence is measured by the emission light detector 30. The processor 38 can repeat the process as desired. The processor 38 assigns a digital value of intensity to each individual LED 24 and relays this address information to the memory device 42, so that the memory device can form a correlation between each individual LED 24 and a digital memory location. These values are read by the digital to analog converter 68 and are subsequently used as a reference to drive the current source 66 that supplies current to the LED 24 selected by the processor 38.

Figure 4:
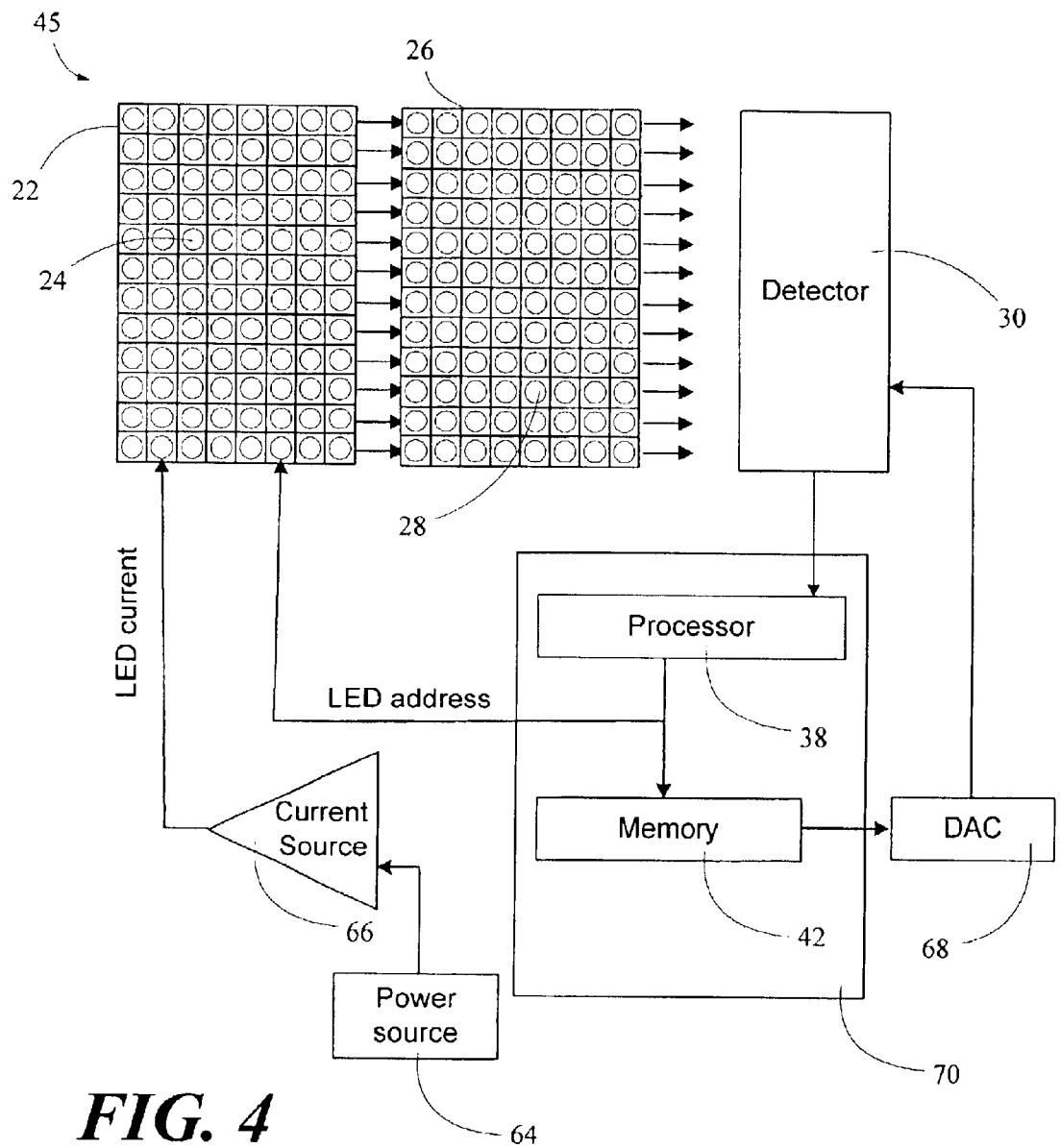
FIG. 4 is a diagrammatic illustration of a controller according to another aspect of the present invention.

An alternative fluorometer 45 configuration is shown in FIG. 4. In this configuration, the controller 70 is used to adjust the gain of the emission light detector 30 for each well 28 position. In situations where the excitation light is difficult to control, the same normalized detection efficiency for each well can be achieved by altering the detector 30 gain for each well 28 position. Examples of methods for altering the detector 30 gain include changing a PMT dynode/cathode potential, changing an avalanche photodiode bias voltage, or changing the amplifier gain after the emission light detector 30.

The fluorometer 45 of FIG. 4 can equalize signal levels, obviating downstream processing of the data from the different wells to obtain normalized response. In addition, post detector noise can be equalized for all wells. However, detector linear range and noise is not equalized.

Figure 5:
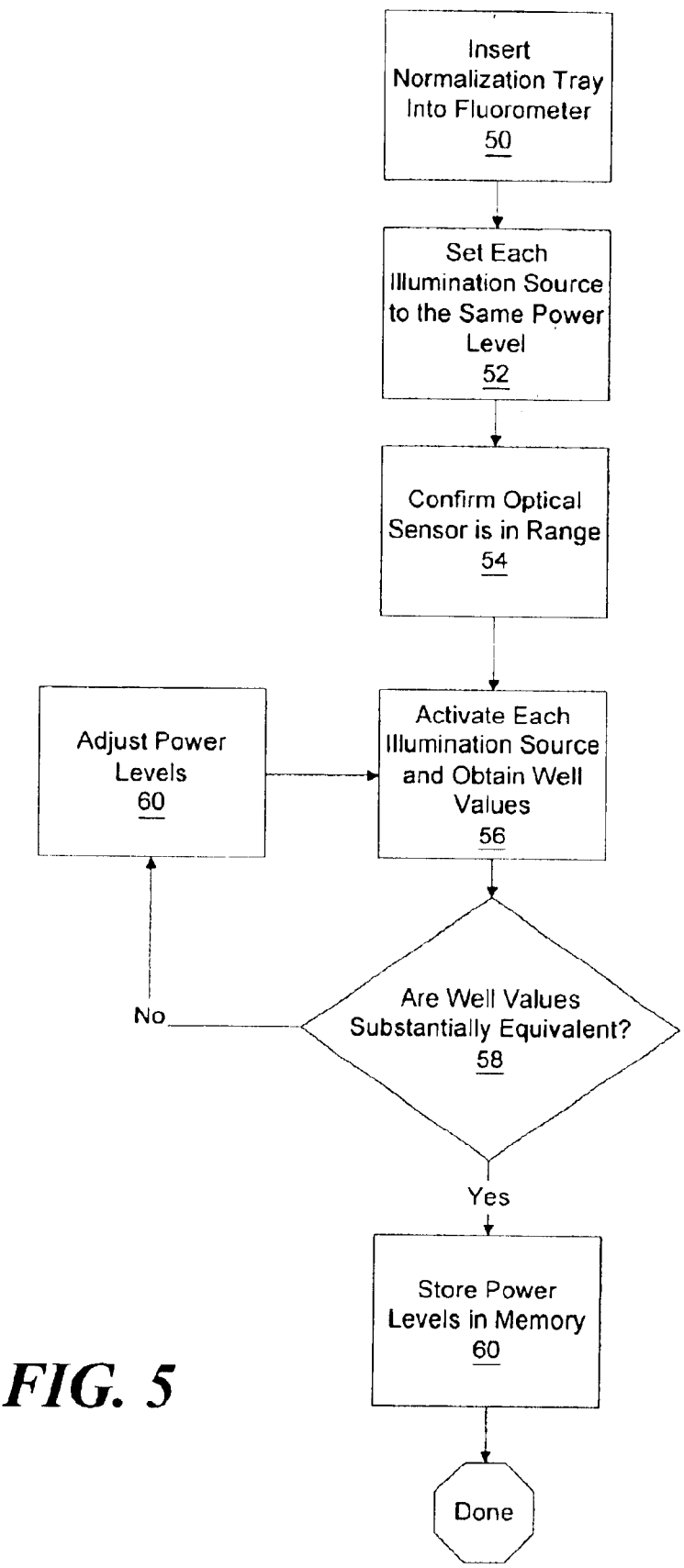
FIG. 5 is a flow chart illustrating the determination of excitation light source power levels according to one aspect of the present invention.

FIG. 5 illustrates one example method used in manufacturing a fluorometer 44 according to the teachings of the present invention. As discussed above, applying equal power levels sequentially to each LED 24 in the LED array 22 with a known and equal quantity of fluorophore in the array 26 of corresponding wells 28 results in non-equal levels of emission light detected by emission light detector 30. This non-uniformity results primarily from geometrical differences in the paths traveled by the excitation and emission light, and is further affected by imperfections in the manufacturing process. Previous solutions to this problem included carrying out a fluorescence measurement using the non-uniform fluorometer, and multiplying all results by a derived normalization factor to obtain a comparable data set. If substantial normalization factors were necessary to even out the detected fluorescent response, substantial different noise levels may be present in the data from the various wells 28, causing variation in the signal-to-noise ratios for the various wells 28.

Therefore, the calibration of the power level of each individual LED 24 is desirable to avoid the need for multiplying resulting data by normalization factors. Calibration of the LEDs 24 can occur as follows. First, a normalization sample or samples in the form of a normalization tray (for example, a tray filled with fluorescence standards, other control samples, or a tray having predetermined empty positions) is inserted into the fluorometer (step 50). The normalization tray can be in the form of the tray 26 with an equal amount of fluorophore in each well. The processor 38 sets each LED 24 at the same initial power level, for example 15 milliamps (step 52). The processor 38 activates individual LEDs 24 and the emission light detector 30 obtains readings to confirm that the fluorescent emissions are within the linear range or the emission light detector 30 (step 54). If the light is outside of the linear range of the emission light detector 30, the gain of the emission light detector 30 (in the case of a PMT) is adjusted, either up or down, to avoid detector saturation or the lower detection limit and move the signal to the middle of the dynamic range. If a different emission light detector 30 technology is used, one of ordinary skill in the art will understand that the range of such detector technology will be adjusted accordingly.

Following gain adjustment, the processor 38 again individually activates each LED 24 and fluorescent measurements of each well of the normalization tray are obtained (step 56) from the emission light detector 30. The processor 38 then compares measured fluorescence from each well to determine whether they are substantially equal (step 58). The term "substantially equal" in this instance is intended to mean within an acceptable range of equality depending on the particular application of the LED array 22. For example, in the current embodiment, an acceptable range of equality is a fluorescence signal variation of ±5%. In other embodiments, an acceptable range of equality may be a fluorescence signal variation of ±2%, ±1%, or even ±0.1%.

Figure 6:
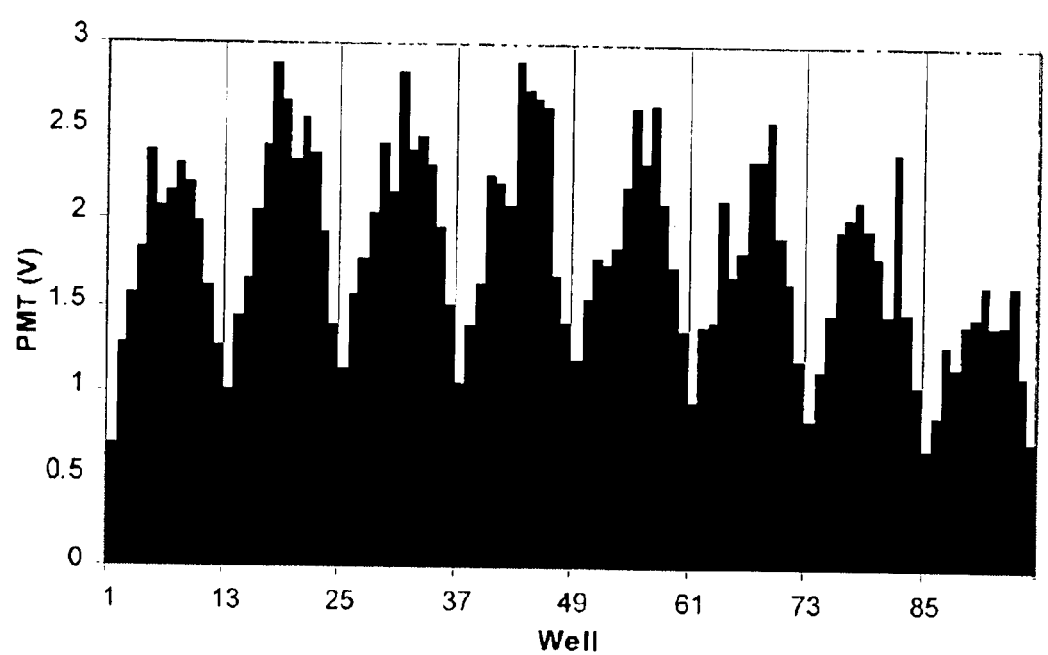
FIG. 6 is a graph plotting optical signal versus excitation light source number prior to normalization according to one aspect of the present invention.

An example comparison, e.g., step 58, of optical signals is shown in FIG. 6, where the fluorescence readings represented by each individual bar of the graph. The optical signals resulting from application of equal power to each LED 24 are substantially different from one another. In the example, the comparison step (e.g., step 58) yields a "No" result, and in adjusting power levels (e.g., step 60) the processor 38 adjusts the power levels to each LED 24. The current to the LEDs 24 is increased for the LEDs 24 having correspondingly low well fluorescence measurements on the graph 46. If an upper current limit for the given LEDs 24 is approached, the current to the entire LED array 22 is slightly lowered by about the same scale. For example, the range of allowable currents is often between 4 mA and 55 mA for LEDs 24 suitable for use with the present invention. This range is dependent on the actual LED and duty cycle, and can vary with manufacturer. An alternative approach may follow the logic that if the well fluorescence measurements are relatively high, the power levels to the LEDs 24 correlating to high well fluorescence measurements are lowered. If the well fluorescence measurements are relatively low, the power levels to LEDs 24 having low fluorescence measurements are raised.

Figure 7:
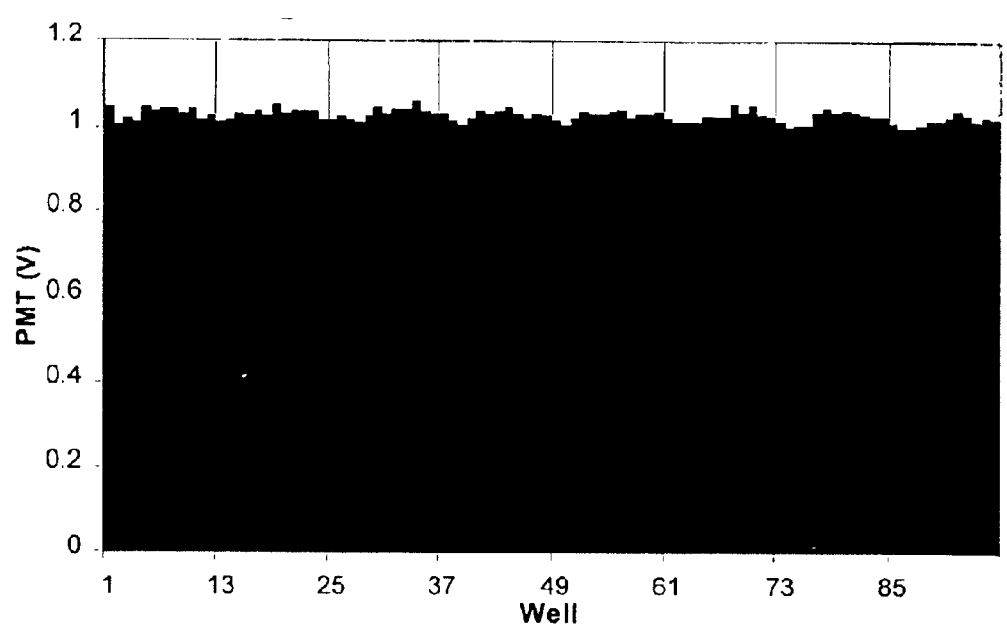
FIG. 7 is a graph plotting optical signal versus excitation light source number after normalization according to one aspect of the present invention.

Following power level adjustment (step 60), each LED 24 is again individually activated and fluorescence measurement of each well is obtained (step 56) using the emission light detector 30. Each fluorescence measurement from each well is again compared to determine whether they are substantially equal (step 58). The process repeats for several iterations in a typical scenario, until the well fluorescence measurements are substantially equal. FIG. 7 illustrates such a condition where each well's fluorescence measurements are substantially equal (within ±5%), which is illustrated as a substantially even line of bars. Once the well values are substantially equal, the processor 38 records the specific power level to each LED 24 in the memory device 42 (step 62).

For most applications, it is desirable to have each LED 24 produce an amount of excitation light, such that the fluorescence from an array of samples containing an equal amount of fluorophore produces a substantially equal response from the emission light detector 30. However, the manufacturing process of the present invention can set each LED 24 to illuminate at any arbitrary level. For example, it might be desirable to increase the dynamic range of the fluorometer by having half of the LED array 22 have low intensity, and the other half of the LED array 22 have a high intensity, so that paired samples will be illuminated at two different levels. Such an arrangement is possible using the method of the present invention.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

What is claimed is:

1. A fluorescence excitation light control system, comprising:
   a controller in communication with a plurality of excitation light sources, the controller comprising:
   a processor controllingly coupled to the plurality of excitation light sources, and
   a memory device for storing data, the memory device being in communication with the processor;
   wherein the controller, in response to at least the data from the memory device, separately controls an intensity of light emitted from each of the excitation light sources to achieve an approximately normalized detection efficiency for a plurality of fluorescent samples.

2. The fluorescence excitation light control system according to claim 1, wherein the controller, in response to at least the data from the memory device, separately controls the intensity of the excitation light sources to approximately conform to a predetermined pattern.

3. The fluorescence excitation light control system according to claim 1 or claim 2, wherein the excitation light sources comprise light-emitting diodes.

4. A fluorometer, comprising:
   a plurality of excitation light sources disposed to emit excitation light toward a plurality of positions for holding a plurality of samples;
   at least one emission light detector disposed to detect light emitted from the plurality of positions; and
   a fluorescence excitation light control system having a controller in communication with the plurality of excitation light sources, the controller comprising:
   a processor controllingly coupled to the excitation light sources; and
   a memory device for storing data, the memory device being in communication
   with the processor;
   wherein the controller, in response to at least the data from the memory device, separately controls an intensity of each of the excitation light sources to achieve an approximately normalized detection efficiency for a plurality of fluorescent samples.

5. The fluorometer according to claim 4, wherein the controller, in responding to at least data from the memory device, separately controls the intensity of the excitation light from each of the plurality of excitation light sources to approximately conform to a predetermined intensity pattern.

6. The fluorometer according to claim 4 or claim 5, further comprising means for collecting fluorescence intensity data received from the emission light detector, and means for providing the fluorescence intensity data to the memory device, wherein the data from the memory device is calculated from the fluorescence intensity data received from the emission light detector.

7. The fluorometer according to claim 4 or claim 5, wherein the emission light detector comprises a photomultiplier tube.

8. A fluorometer comprising:
a plurality of positions for holding a plurality of samples;
at least one emission light detector disposed to detect light emitting from the plurality of positions;
a controller in communication with a plurality of excitation light sources disposed to emit light toward the plurality of positions, the controller comprising:
a processor controllingly coupled to the excitation light sources; and
a memory device for storing data, the memory device being in communication with the processor;
wherein the controller, in response to at least the data from the memory device, separately controls an excitation light intensity from each of the excitation light sources to achieve an approximately normalized detection efficiency for the plurality of samples.

9. The fluorometer according to claim 8, wherein the plurality of positions for holding the plurality of samples comprises a plurality of wells disposed in an array configuration.

10. The fluorometer according to claim 9, wherein the plurality of excitation light sources comprises a plurality of light-emitting diodes disposed in an array configuration.

11. The fluorometer according to claim 10, wherein each of the plurality of excitation light sources is in optical communication with substantially only one of the plurality of wells.

12. The fluorometer according to claim 8, wherein the plurality of excitation light sources comprises a plurality of light-emitting diodes disposed in an array configuration.

13. The fluorometer according to claim 8, claim 9, claim 10, claim 11, or claim 12, wherein the emission light detector comprises a photomultiplier tube.

14. A method of manufacturing a fluorometer comprising a plurality of independently-controllable excitation light sources, the method comprising:
placing a normalization sample in optical communication with excitation light sources;
operating the excitation light sources with a predetermined power level;
measuring fluorescence emission from the normalization standards; and
adjusting power levels of the excitation light sources to achieve a desired normalization.

15. The method of claim 14, wherein the normalization sample comprises one or more fluorescence standards.

16. The method of claim 15, wherein adjusting the power levels of the excitation light sources is performed so as to normalize the detection efficiency for the one or more fluorescence standards.

17. A method of manufacturing a fluorometer, the method comprising:
placing a plurality of normalization samples into a plurality of wells;
using a controller to control excitation light sources to achieve a predetermined pattern of excitation light intensity;
measuring fluorescence emission from the plurality of normalization samples; and
altering data in a memory device of the fluorometer to achieve a pattern of excitation light intensity that results in an approximately normalized detection efficiency for the plurality of normalization samples.

18. The method of claim 17, wherein altering the data in the memory device comprises programming an EEPROM with digital values corresponding to power levels.

19. A fluorometer, comprising:
a plurality of positions for holding a plurality of samples;
a fluorescence excitation light source disposed to individually illuminate the plurality of samples;
at least one emission light detector system, comprising:
at least one emission light detector disposed to detect light emitted from the plurality of positions;
a processor controllingly coupled to the fluorescence excitation light source and also coupled to the at least one emission light detector or to an amplifier of a signal from the at least one emission light detector; and
a memory device for storing data, the memory device being in communication with the processor;
wherein the processor, using data from the memory device, separately controls a gain of the signal from the at least one emission light detector for each of the plurality of samples illuminated by the excitation light source to achieve an approximately normalized detection efficiency for a plurality of fluorescent samples.

* * * * *